United States Patent [19]
Gundlach et al.

[11] Patent Number: 5,242,454
[45] Date of Patent: Sep. 7, 1993

[54] METHOD FOR DIAGNOSIS AND SHOCK WAVE LITHOTRIPSY OF STONES IN THE SUBMAXILLARY AND PAROTID GLANDS

[75] Inventors: Peter Gundlach; Jurgen U. G. Hopf, both of Berlin, Fed. Rep. of Germany

[73] Assignee: Omega Universal Technologies, Ltd., London, United Kingdom

[21] Appl. No.: 898,017

[22] Filed: Jun. 12, 1992

[51] Int. Cl.$^5$ ............................................. A61B 17/22
[52] U.S. Cl. ................................... 606/128; 128/898; 606/127
[58] Field of Search ............. 128/898, 24 EL, 24 AA; 606/1, 2, 3, 106, 110, 113, 127, 128

[56] References Cited

U.S. PATENT DOCUMENTS

| | | |
|---|---|---|
| 4,887,600 | 12/1989 | Watson et al. ...................... 606/128 |
| 4,932,954 | 6/1990 | Wondrazek et al. ................ 606/128 |
| 4,939,336 | 7/1990 | Meyer et al. . |
| 5,009,658 | 4/1991 | Damgaard-Iverson et al. .... 606/128 |
| 5,041,121 | 8/1991 | Wondrazek et al. ............... 606/128 |
| 5,059,200 | 10/1991 | Tulip .................................... 606/128 |
| 5,074,867 | 12/1991 | Wilk .................................... 606/128 |

Primary Examiner—Stephen C. Pellegrino
Assistant Examiner—Glenn Dawson
Attorney, Agent, or Firm—Herbert W. Larson

[57] ABSTRACT

A 1.4-1.6 mm diameter microendoscope is introduced into a duct leading to the submaxillary or parotid glands containing a concrement. The endoscope is adapted to contain a working channel, an image bundle, a light bundle and a wire, all structure fixedly spaced apart within the microendoscope. A laser fiber is inserted into the working channel to the concrement and the concrement is fragmented with a laser shock wave while flushing the fragments away through the working channel.

10 Claims, 2 Drawing Sheets

METHOD FOR DIAGNOSIS AND SHOCK WAVE LITHOTRIPSY OF STONES IN THE SUBMAXILLARY AND PAROTID GLANDS

BACKGROUND OF THE INVENTION

1. Field of The Invention

This invention relates to methods for diagnosis and lithotripsy to fragment calculi under direct endoscopic vision. More particularly, it refers to a method of reaching the submaxillary and parotid glands to fragment calculi via the gland ducts.

2. Description of the Prior Art

Procedures are now well known to fragment human stones in the gall bladder, kidney and ureter using endoscopic lithotripsy. A laser fiber is delivered through a fiber optic probe passed along into a normal size (4-10 mm) rigid or flexible scope. Either a pulsed dye laser or Q-switched NdYAG laser is used in the procedure. See U.S. Pat. Nos. 4,932,954; 5,059,200; and 5,009,658. Stones also occur in other hard to penetrate areas such as the submaxillary and parotid glands. Lithotripsy procedures heretofore used to fracture stones in the gall bladder, kidney and ureter cannot be used to fracture stones in the submaxillary and parotid glands because of the unusually narrow diameter of the ducts leading to these glands. Consequently, invasive surgical procedures are now used to remove these two glands with the concrement. A procedure is needed to remove concrements or stones in the submaxillary and parotid glands without resorting to surgery.

SUMMARY OF THE INVENTION

We have discovered a method of minimally penetrating the submaxillary and parotid glands to fragment calculi using improved procedures and microendoscopic equipment.

Our method is employed using a flexible microendoscope containing an actively steerable or articulation mechanism, a light guide fiber optic arrangement, an image guide bundle and lens and a working or flushing channel, all being permanently positioned spaced apart by epoxy resin inside a polyurethane or polytetrafluoroethylene jacket. A topical anesthetic is applied to the gland and a dilating probe is introduced into the salivary duct and the papilla which is gradually dilated by dilators of increasing size. One to two ml of an anesthetic is additionally instilled in the salivary duct using a suitable size sialography catheter. A microendoscope having a diameter between 1.4–1.6 mm is then introduced into the gland and advanced to the stone under visual guidance while isotonic saline solution is flushed in continuously with slight pressure via the working channel to dilate the lumen. Mucous, thickened or purulent secretion is drained via the working channel whose size is not less than 0.5 mm.

A 200 mm laser photoconductor or any other suitable size lithostriptor probe is then positioned on the stone via the working channel and the concrement is fractured by a laser induced shock wave or electrohydraulic energy under continuous rinsing. The stone particles are either rinsed or drained off or leave the salivary duct by the re-channelized salivary flow.

BRIEF DESCRIPTION OF THE DRAWINGS

The invention may be best understood by those having ordinary skill in the art by reference to the following detailed description when considered in conjunction with the accompanying drawing in which.

DETAILED DESCRIPTION OF THE INVENTION

Figure 1:
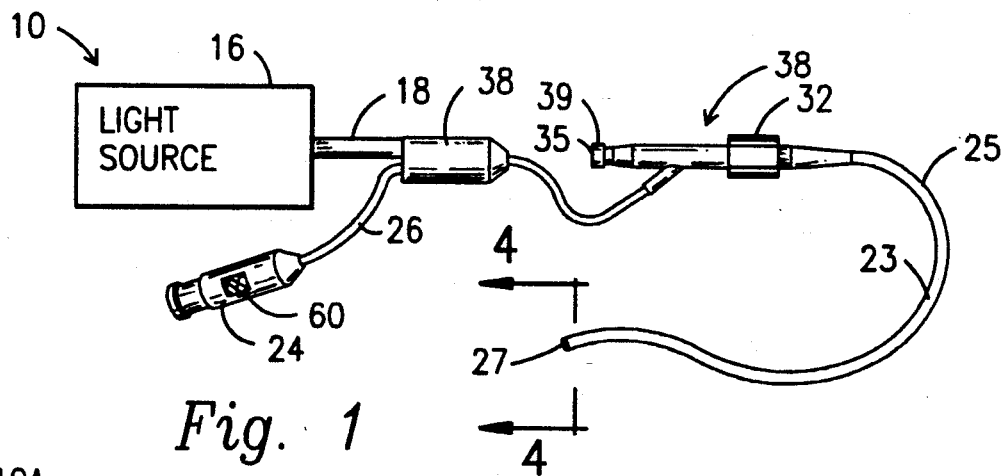
FIG. 1 is a schematic view of the equipment used to carry out our method.

Throughout the following detailed description, the same reference numerals refer to the same elements in all figures.

Figure 4:
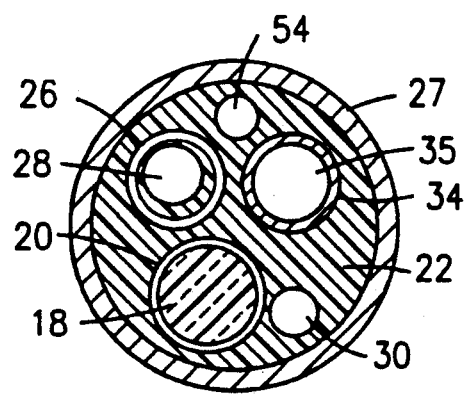
FIG. 4 is a sectional view through line 4—4 of the microendoscope distal end.
Figure 5:
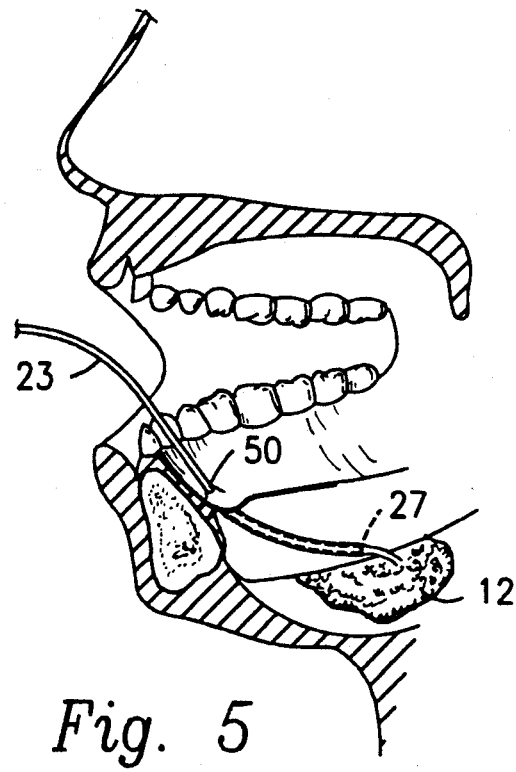
FIG. 5 is a lateral sectional view through a patient's jaw showing the microendoscopic in the submaxillary gland.

The microendoscopy apparatus 10 shown in FIG. 1 is used for diagnosis and as a delivery conduit of the shock wave pulses generated by a laser or an electrohydraulic device to fracture salivary stones. These concrements or stones 12 can be in the submaxillary gland, seen in FIG. 5, or the stones 14 can be in the parotid gland, shown in FIG. 6. The microendoscopy apparatus 10 used in this method employs a light source 16 which is linked to a 45-50 light guide fiber array 18, as shown in FIG. 4. The fibers are encased in an extruded polytetrafluoroethylene or polyurethane jacket 20. The jacket 20 is prevented from moving by an epoxy encasement 22. The epoxy 22 spaces apart the various channels or bundles of fibers contained within the microendoscope 23. The microendoscope 23 also has a polytetrafluoroethylene or polyurethane jacket 25. A stainless steel tube 27 of 3 mm length at the distal end is designed to encase channels for video capacity. A magnification eyepiece 24 is connected to an image guide bundle 26 containing 4000–5000 pixels and the image guide grin lens 28 with a 70° degree angle of view shown in FIG. 4. A focus adjustment 60 is located on eyepiece 24. An articulation wire 30 attached to a handle 32 is also mounted within the apparatus 10. Lastly, a flush channel 35 is encircled within the epoxy 22 and also acts as the working channel conduit 35 for the working apparatus. A polytetrafluoroethylene covering 34 encloses channel 35. A branch coupler 38 unites the individual channels for the imagee bundle 26 and light bundle 18. Working channel 35 starts at opening 39 and articulation wire 30 is controlled in the body of the microendoscope 23 by handle 32.

Figure 2:
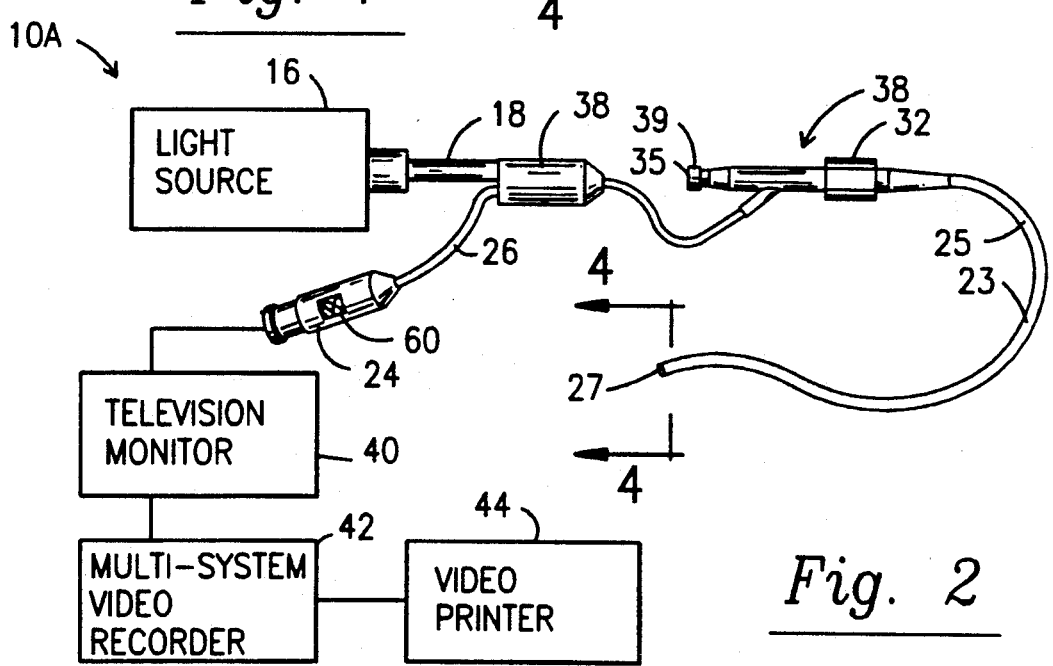
FIG. 2 is a schematic view of the eyepiece and internal gland visual representation equipment employed in our method.
Figure 3:
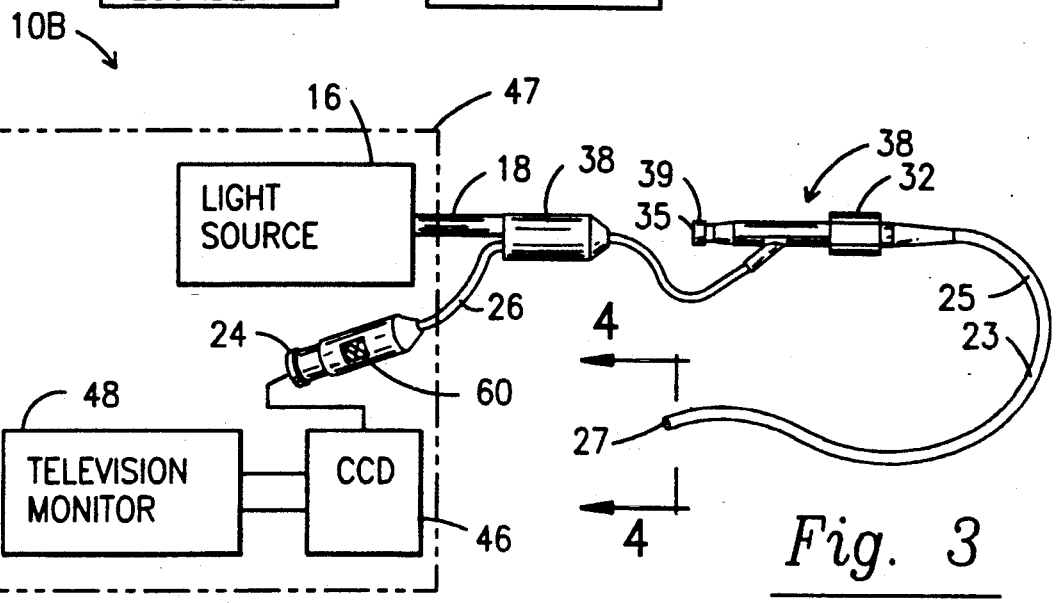
FIG. 3 is a schematic view of an alternate embodiment for the diagnostic procedure employing a television monitor.

Optionally, as seen in FIG. 2 the apparatus 10A includes a television monitor 40 attached to the eyepiece. This monitor 40 connected to a multi-system video recorder 42 and a video printer 44 as separate modules. Still further, as seen in FIG. 3 the apparatus 10B includes charge coupled device (CCD) 46 attached to the eyepiece 24 and this CCD can be directly connected to a television monitor 48 for viewing the movement of the working channel 35, within the body of the patient. This whole system with components 48, 46 and 16 can be enclosed in a housing 47.

The method is carried out by first introducing a dilation probe (not shown) into the salivary duct 50. The papilla is dilated by dilators of increasing size. Thereafter, the flexible microendoscope 23 having a diameter of about 1.4–1.6 mm is introduced into the duct 50 and advanced to the concrement 12 under visual guidance through image bundle 26. The area is illuminated by the light source 16 through the fiber optic 18 light guides. A laser photo conductor of size 0.2 mm–0.3 mm is then positioned on the stone 12 via the working channel 35. The working channel 35 has an outer diameter of 0.5 mm. The concrement is fractured by a laser induced shock wave under continuous rinsing and flushing through the surrounding 0.3–0.77 mm area around the photoconductor. Stone fragmented particles are either rinsed or drained off or leave the salivary duct by the re-channeled salivary flow. Three short-pulse systems can be used. These are the Excimer having a wave length of 308 nm and pulse length FWHM 60 ns; a Dye Laser having a wave length of 504 nm and pulse length of FWHM 1200 ns; and an Alexandrite Laser having a wave length of 755 nm and a pulse length FWHM of 300 to 500 ns.

Carrying out the method of this invention, the sialolithiasis is performed on out-patient basis while the patient is lying prone. The patient is unsedated. The head is slightly hyper extended to give the Examiner a direct view of the oral cavity and the ostia of the salivary duct. After infiltration anaesthesia and administration of a local surface anaesthetic, the probe is introduced into the salivary duct. 1 to 2 ml of an anaesthetic is additionally instilled in the salivary duct via a sialography catheter to block sensory afferences of the area. During the advancement of the flexible microendoscope 23, isotonic saline solution is flushed in continuously through the working channel 35. Use of the isotonic solution prevents soiling of the lens 28 attached to the silica image bundle at the distal end of the microendoscopic channel 26 in the stainless steel tip 27. Also, a better view of the lumen is gained by distension of the salivary duct. Mucous, thickened or purulent secretion is drained via the working channel. Secretion plugs can be immobilized, dissolved and drained by controlled forced rinsing.

Figure 6:
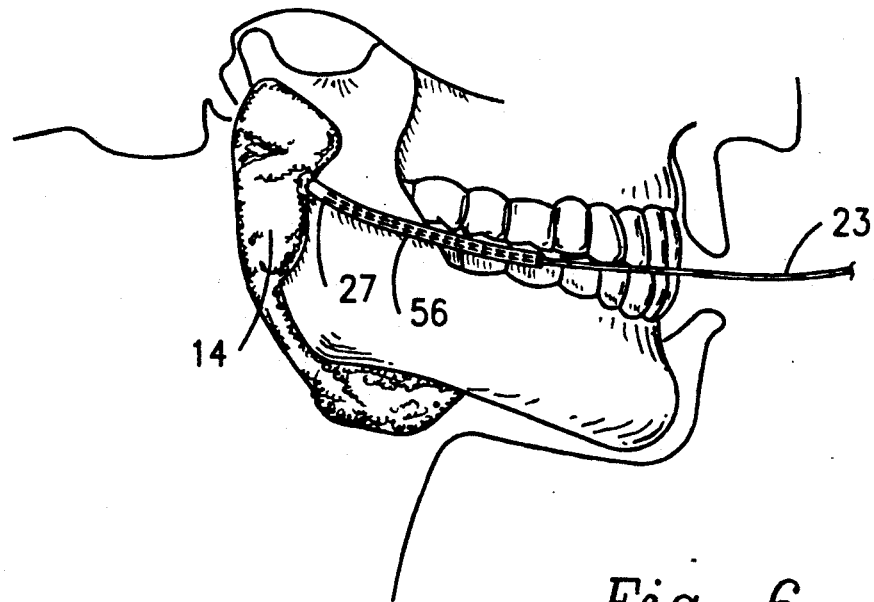
FIG. 6 is a lateral sectional view through a patient's jaw showing penetration of the parotid gland.

During introduction of the microendoscope 23 into the salivary duct 50, the articulation wire 30 is controlled by handle 32 so that the tip 27 at the end of the microendoscope 23 can be deflected as necessary by the operating physician up to 90 degrees to position the microendoscope 23 adjacent the stones 12 to be fractured. The same procedure is followed, as shown in FIG. 6, to penetrate the parotid gland duct 56 and fracture stone 14. A point marker 54 is located at the distal end in tip 27 to provide an orientation marker for the operating physician.

Having thus described the invention, what is claimed and desired to be secured by Letters Patent is:

1. A method for diagnosing in a patient a presence of a concrement and fragmenting the concrement located in a submaxillary or parotid gland comprising
   (a) introducing multiple dilation probes of increasing size into the papilla of the gland,
   (b) penetrating a duct leading to the gland with a microendoscope having an outside diameter of 1.4–1.6 mm,
   (c) the microendoscope adapted to contain a working channel, an image bundle, a light bundle and an articulation wire, all fixedly spaced apart by a thermosetting medium,
   (d) advancing the microendoscope to the concrement under visual guidance by employing the image bundle while illuminated from a light source employing the light bundle,
   (e) introducing a laser photoconductor having a diameter of about 0.2 to 0.3 mm through the working channel to a position adjacent the concrement,
   (f) fracturing the concrement by a laser induced shock wave while continuously rinsing an area around the photoconductor with fluid introduced through the working channel to remove concrement fragments, and
   (g) the articulation wire being continuously moved by a handle outside the microendoscope to guide a distal tip of the microendoscope through the duct to the concrement and positioning the laser at its most advantageous point on the concrement.

2. A method according to claim 1 wherein the patient is lying prone and unsedated and a local surface anaesthetic is introduced into the duct prior to dilation with 1 to 2 ml of an anaesthetic additionally instilled in the duct by a sialography catheter.

3. A method according to claim 1 wherein isotonic saline solution is flushed continuously through the working channel during advancement of the microendoscope towards the concrement.

4. A method according to claim 1 wherein the tip of the microendoscope is articulated up to 90 degrees.

5. A method according to claim 1 wherein the thermosetting medium employed to fixedly space apart the channels is an epoxy resin.

6. A method according to claim 1 wherein the microendoscope is adapted to have an outside covering of polytetrafluoroethylene.

7. A method according to claim 1 wherein the microendoscope is adapted to have an outside covering of polyurethane.

8. A method according to claim 1 wherein the laser induced shock wave comes from an Excimer laser having a wave length of about 308 nm and a pulse length FWHM of about 60 ns.

9. A method according to claim 1 wherein the laser induced shock wave comes from a Dye laser having a wave length of about 504 nm and a pulse length FWHM of about 1200 ns.

10. A method according to claim 1 wherein the laser induced shock wave comes from an Alexandrite laser having a wave length of about 755 nm and a pulse length FWHM of about 300 to 500 ns.

* * * * *